(12) United States Patent
Chang et al.

(10) Patent No.: US 9,033,979 B2
(45) Date of Patent: May 19, 2015

(54) ARTICULATING ABLATION AND DIVISION DEVICE WITH BLOOD FLOW SENSING CAPABILITY

(75) Inventors: Stephen Kin Yong Chang, Singapore (SG); Chee Kong Chui, Singapore (SG)

(73) Assignee: National University of Singapore, Singapore (SG)

( * ) Notice: Subject to any disclaimer, the term of this patent is extended or adjusted under 35 U.S.C. 154(b) by 228 days.

(21) Appl. No.: 13/704,560

(22) PCT Filed: Jun. 22, 2011

(86) PCT No.: PCT/SG2011/000221
§ 371 (c)(1),
(2), (4) Date: Dec. 14, 2012

(87) PCT Pub. No.: WO2011/162724
PCT Pub. Date: Dec. 29, 2011

(65) Prior Publication Data
US 2013/0085497 A1    Apr. 4, 2013

Related U.S. Application Data

(60) Provisional application No. 61/344,283, filed on Jun. 23, 2010.

(51) Int. Cl.
| | |
|---|---|
| *A61B 18/14* | (2006.01) |
| *A61B 18/08* | (2006.01) |
| *A61B 17/32* | (2006.01) |
| *A61B 18/00* | (2006.01) |
| *A61B 18/18* | (2006.01) |
| *A61B 17/00* | (2006.01) |

(52) U.S. Cl.
CPC ........ *A61B 18/082* (2013.01); *A61B 2018/1455* (2013.01); *A61B 2018/00958* (2013.01); *A61B 2018/00642* (2013.01); *A61B 2018/00708* (2013.01); *A61B 17/32* (2013.01); *A61B 18/1402* (2013.01); *A61B 18/1815* (2013.01); *A61B 2017/00106* (2013.01); *A61B 2017/00544* (2013.01); *A61B 2018/00589* (2013.01); *A61B 2018/143* (2013.01)

(58) Field of Classification Search
None
See application file for complete search history.

(56) References Cited

U.S. PATENT DOCUMENTS

| | | | |
|---|---|---|---|
| 5,423,810 A | 6/1995 | Goble et al. | |
| 5,443,463 A | 8/1995 | Stern et al. | |

(Continued)

FOREIGN PATENT DOCUMENTS

| | | |
|---|---|---|
| WO | WO 97/17014 | 5/1997 |
| WO | WO 02/080796 A1 | 10/2002 |

OTHER PUBLICATIONS

International Search Report for International Application No. PCT/SG2011/000221 filed Jun. 22, 2011.

*Primary Examiner* — Kennedy Schaetzle
(74) *Attorney, Agent, or Firm* — Hamilton, Brook, Smith & Reynolds, P.C.

(57) ABSTRACT

A laparoscopic liver resection device is described. The device combines the Radiofrequency Ablation (RFA) technology with a cutting mechanism, a blood-flow sensor and a flexible actuation mechanism to simultaneously coagulate and cut the liver tissue and detect the presence of blood flow to confirm avascularity. The present invention eliminates the risk of excess bleeding due to cutting too deep and reduces recovery time and the time spent on re-coagulation of coagulated areas, thereby shortening duration of surgery. Also embodiments prevent excess ablation by stopping ablation activity on the target tissue as soon as insufficient or no blood flow in the target tissue is detected. Thus a closed loop control for a bloodless tissue/organ division method is provided.

19 Claims, 3 Drawing Sheets

(56) References Cited

U.S. PATENT DOCUMENTS

| | | | |
|---|---|---|---|
| 5,558,671 A * | 9/1996 | Yates | .............................. 606/38 |
| 5,571,098 A | 11/1996 | Domankevitz | |
| 6,024,741 A | 2/2000 | Williamson, IV et al. | |
| 6,666,854 B1 | 12/2003 | Lange | |
| 2005/0165415 A1 | 7/2005 | Wales | |
| 2008/0114549 A1 * | 5/2008 | Schafer et al. | .................. 702/19 |

* cited by examiner

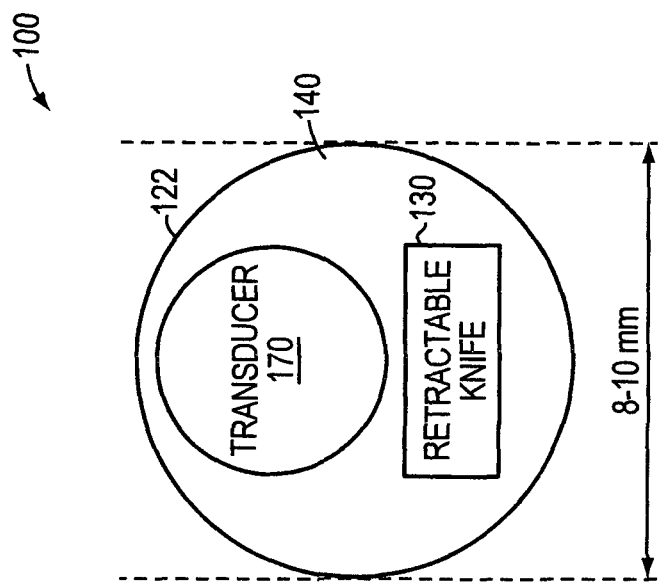
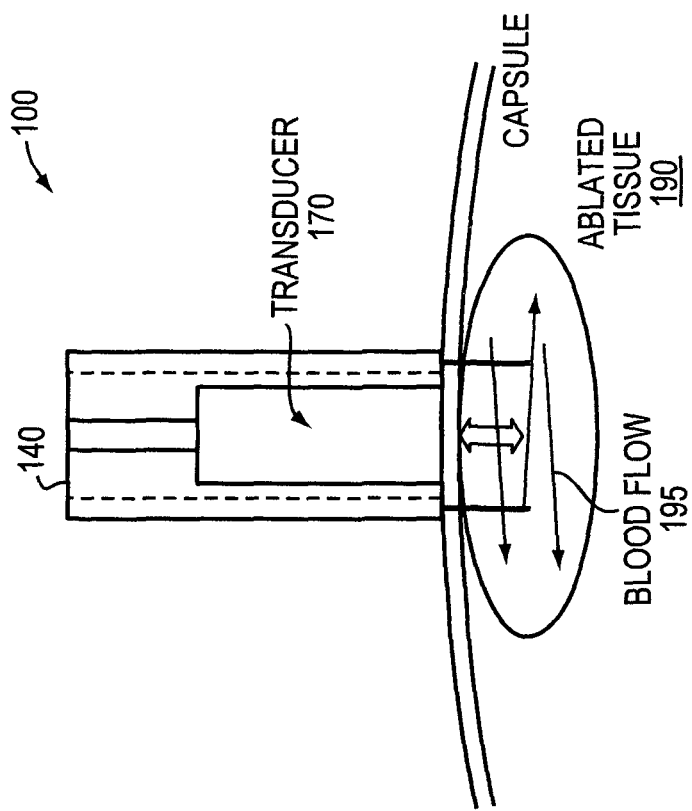

ARTICULATING ABLATION AND DIVISION DEVICE WITH BLOOD FLOW SENSING CAPABILITY

RELATED APPLICATION

This application is the U.S. National Stage of International Application No. PCT/SG2011/000221, filed Jun. 22, 2011, which designates the U.S., published in English, and claims the benefit of U.S. Provisional Application No. 61/344,283, filed Jun. 23, 2010. The entire teachings of the above applications are incorporated herein by reference.

BACKGROUND

Laparoscopic surgery, also referred to as minimally invasive surgery, is a technique that provides access to the abdomen or pelvic cavities through small incisions. In a typical laparoscopic surgery, a laparoscope is used. The laparoscope may be a telescopic rod lens system or a charge-coupled device (CCD) that is coupled with a camera. The abdominal or pelvic cavity is insufflated with a non-flammable gas (e.g., carbon dioxide) and illuminated with a light source using a fiber optic cable system. Due to the small size of the incisions, laparoscopic surgery minimizes post operative pain and speeds the recovery process.

Laparoscopic surgery techniques may be used in resection of the liver to remove portions of the liver. Traditionally, a laparoscopic liver resection surgery involves removal of the liver tumor with a surrounding margin of about half inch of normal liver tissue. The laparoscopic liver resection surgery may only be used for anomalies located on or near the surface since they can be removed without major risk of injury. Removal of tumors that are deeply located within the liver tissue involves higher risk of injury and uncontrolled bleeding from the blood vessels within the substance of the liver.

SUMMARY

Certain embodiments of the present invention relate to a medical device that includes (i) a plurality of coagulating elements that coagulate target tissue of a biological body, (ii) a blood flow sensor that indicates absence of blood flow within the target tissue as coagulated by coagulating elements, and (iii) a retractable cutter that cuts the target (coagulated) tissue in an event of sensed absence of blood flow within the tissue is indicated. The sensor detects blood flow within the target tissue during operation of the coagulating elements on the target tissue. In the event the sensor senses absence of blood flow within the target tissue, this event is indicative of coagulation (or ablation) being complete such that cutting by the retractable cutter may commence and coagulation activity by the coagulating elements may cease. An actuator is coupled to the retractable cutter that actuates the retractable cutter within the coagulated tissue.

Some embodiments relate to a method for dividing the tissue of a biological body where target tissue is acted on so as to become coagulated, and absence of blood flow within the coagulated tissue is sensed. If absence of blood flow within the subject tissue is indicated, the embodiment actuates a retractable cutter to cut the coagulated tissue. In other embodiments, upon detection of absence of blood flow within the target tissue, the method also discontinues coagulating activity/action on the target tissue to prevent against excess ablation.

The blood flow sensor may indicate the absence of blood flow in an event where zero blood flow within the subject tissue (i.e. target tissue as being coagulated by the coagulating elements) is observed. The blood flow sensor may indicate the absence of blood flow in an event the blood flow observed within the subject tissue is less than a predetermined threshold. The blood flow sensor may indicate the absence of blood flow within the subject tissue by evaluating intensity of a backscattered signal resulting from irradiating the tissue with an ultrasonic wave. The blood flow sensor may indicate the absence of blood flow within the subject tissue by evaluating intensity of a backscattered signal resulting from analyzing the tissue using at least one of an ultrasonic wave, a shock wave, mechanical tissue properties, and electrical impedance imaging.

The actuator may be at least one of a pneumatic actuator, a spring, an electrochemical actuator, an electromechanical actuator and a mechanical actuator. The blood flow sensor may continually sense amount of blood flow in the target tissue. The actuator may then actuate the retractable cutter away from the live tissue in an event where presence of blood flow within the sample tissue is indicated (re-established). The actuator may employ one or more electroactive polymers (EAP) actuation elements.

The retractable cutter may be at least one of a retractable knife or a retractable scalpel.

A housing at the distal end of the invention device may house at least the plurality of coagulating elements and the retractable cutter. The distal end may be coupled with at least one flexible structure that provides the distal end with movement in two or more degrees-of-freedom. The flexible structure may be spherical for example.

The plurality of coagulating elements may be needle shaped electrodes, lasers or certain energy waves. The plurality of coagulating elements may coagulate the tissue using at least one of Radiofrequency Ablation (RFA), microwave ablation, cryo ablation, high intensity focused ultrasound ablation, and shockwave ablation of the tissue.

Advantageously, embodiments of the present invention provide in a single instrument (a) reduced risk of unnecessary cutting and resulting bleeding (i.e., reduced blood loss) where a blood flow sensor detects proper coagulation of target tissue before cutting, and (b) reduced exposure (number of incisions and time duration of procedure) where integrated cutting device and coagulating elements are arranged in a flexible distal end having multiple degrees of freedom and are operated under guidance of the sensor feedback. There is also the advantage of embodiments preventing excess ablation by stopping the ablation as soon as insufficient or no blood flow in the target tissue is detected by the blood flow sensor. Thus some embodiments provide a closed loop control for a bloodless tissue/organ division method.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 1A-1D illustrate a laparoscopic liver resection device 100 according to certain embodiments of the present invention.

DETAILED DESCRIPTION

Figure 1B:
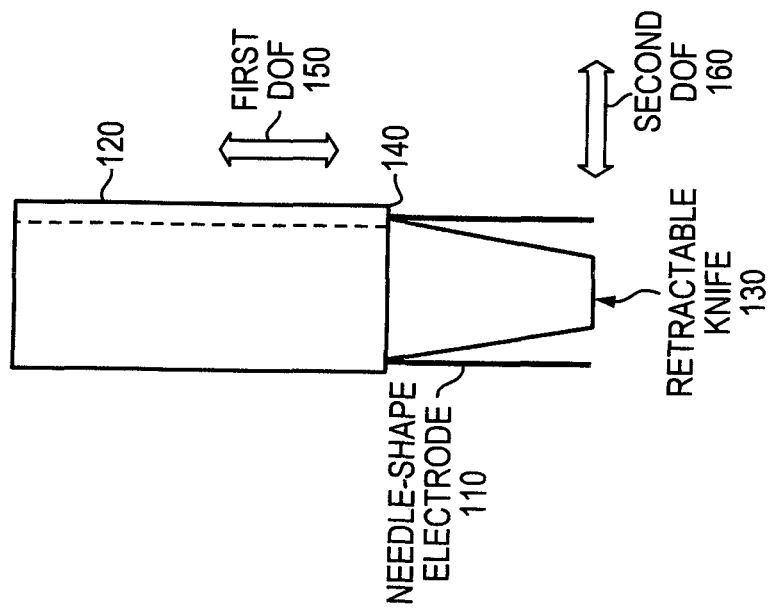

A description of example embodiments of the invention follows.

Embodiments of the present invention relate to a medical device that may be used to simultaneously coagulate and cut biological tissue. Embodiments of the present invention may be used to perform various medical procedures across various areas of a biological body (e.g., liver, abdomen cavity, and pelvic cavity). Although the terms "liver resection" and "laparoscopic resection" are used herein to describe example embodiments of the invention, one skilled in the art recognizes that the embodiments of the present invention are not limited to liver resection and/or laparoscopic surgery of the liver and may be used in a wide range of operations/applications (medical procedures generally).

The term "operation," as used herein, is a broad term that is used in its ordinary sense, including, without limitation, to refer to manual, guided, or instrumental techniques for investigating and/or treating a pathological condition such as disease or injury or to help improve certain body features and/or conditions (e.g., appearance). The term "operation," as used herein, may refer to any procedures or operation techniques known in the art, such as laparoscopic surgery.

Certain embodiments of the present invention relate to a laparoscopic medical device that integrates a tissue coagulation mechanism, a blood flow sensing mechanism, a flexible actuation mechanism, as well as a tissue cutting mechanism to reduce blood loss and duration of a procedure.

Other embodiments provide a closed loop control for a bloodless tissue/organ division method. Excess ablation is prevented by the method/system stopping the ablation as soon as insufficient or no blood flow in the target tissue is detected.

Embodiments of the present invention may be used in a wide range of applications, such as resection. The term "resection," as used herein, is a broad term that is used in its ordinary sense, including, without limitation, to refer to removal of tissue, lesion, and/or one or more organs from a biological body. For example, certain embodiments of the invention may be used in liver resection. Liver resection is the most effective mode of curative treatment for liver tumors and neoplasm. Unfortunately, there are various issues with liver resection among which bleeding is the most significant issue. Other issues include difficulties in exposing the liver during surgery, and the invasiveness of open liver resections. Although laparoscopic liver resection has solved the latter issues, bleeding is still considered the most significant issue associated with liver resection.

To address the problem of bleeding, various special devices have since been developed. Currently, some of the more commonly used devices in liver resection include the Cavitron Ultrasonic Surgical Aspirator (CUSA), harmonic scalpel, and radiofrequency ablation (RFA)-assisted devices. Although these devices have been shown to improve the ability to control bleeding, these devices each have their own associated disadvantages.

For example, the CUSA is an ultrasonically powered device that selectively fragments and aspirates liver tissues while sparing blood vessels and connective tissues. This is possible as the rate of its cavitational activity is proportionate to the water content of the cells. Therefore, tissue damage is confined to an area of about 25 to 50 micrometer next to the tip and is minimal as compared to resection using scalpel or lasers. (Yao P, Gunasegaram A, Ladd L A, Chu F, Morris D L. In Line radiofrequency ablation-assisted laparoscopic liver resection: first experiment with stapling device. *ANZ J Surg*. 2007 June; 77(6):480-4.) However, the long probe of this device makes it difficult for use in laparoscopic liver surgery and is, therefore, more suitable for open liver resections.

The harmonic scalpel is an ultrasonic cutting and coagulating surgical device that cuts and coagulates at temperatures ranging from 50° C. to 100° C. The blade vibrates at 55,500 Hz and denatures protein in the tissues to form a sticky coagulum. As pressure is applied on tissues with the blade surface, blood vessels collapses and allows the coagulum to form a hemostatic seal preventing bleeding. (Johnson & Johnson Gateway. Harmonic Scalpel Technology Overview. Available at: www.jnjgateway.com/home.jhtml;jsessionid= ILYBTXE4S4MWOCQPCCGWPOIKB2IIWTT1?loc= USENG&page=viewContent&contentId= 09008b9880a2d37a&parentId=09008b9880a2d37a, Accessed Dec. 5, 2007.) However, the control of bleeding with this device is not optimal.

In order to address the problem of bleeding, some embodiments of the present invention may employ various tissue coagulation mechanisms. The term "coagulation," as used herein, is a broad term that is used in its ordinary sense, including, without limitation, to refer to forming blood clots. Various coagulation techniques known in the art may be used. For example, some embodiments may use Radio frequency ablation (RFA) to coagulate tissue prior to cutting. In certain other embodiments, thermal coagulation, microwave ablation, laser-based ablation, shockwave ablation, cryo ablation, high intensity focused ultrasound ablation and/or other coagulation methods known in the art may be used.

RFA is a form of thermal ablation technique commonly used for local control of unresectable liver tumors. The RFA uses high frequency alternating currents in electrodes to produce ionic agitation within the surrounding tissues. The highest temperature is found in the tissues closest to the electrodes and the localized friction heat results in localized areas of coagulative necrosis. (National Institute for Health and Clinical Excellence. Radiofrequency Ablation of Hepatocellular Carcinoma. Available at: www.nice.org.uk/guidance/ index.jsp?action=byID&r=true&o=11082, Accessed Dec. 5, 2007; and Galandi D, Antes G. Radiofrequency Thermal Ablation versus Other Interventions for Hepatocellular Carcinoma. United Kingdom, UK: John Wiley and Sons; 2004.) Cooling and temperature control mechanisms, such as internal water cooling of probes are present to prevent over heating of tissues, which will lead to their desiccation, and prematurely halt the ablation process.

The RFA-assisted laparoscopic liver resection has been used in the past to deal with the bleeding associated with liver resection. Studies have shown that RFA-assisted laparoscopic liver resection results in reduced blood loss during operations (Ayav A, Bachellier P, Habib N A, et al. Impact of radiofrequency assisted hepatectomy for reduction of transfusion requirements. *Am J Surg*. 2007 February; 193(2):143-8). The RFA has been used to assist in liver resection because of its ability to create an avascular plane. (Milićević M, Bulajić P, Žuvela M, Dervenis C, Basarić D, Galun D. A Radiofrequency-Assisted Minimal Blood Loss Liver Parenchyma Dissection Technique. *Dig Surg*. (2007) 24:306-313. Available online from: library.sheba.co.il:8080/Karger/Produkt-eDB/produkte.asp?Aktion=ShowPDF&ArtikelNr= 103663&Ausgabe=233196&ProduktNr= 223996&filename=103663.pdf Assessed Dec. 1, 2007.) In RFA-assisted laparoscopic liver resection, the liver parenchymal is first coagulated with RFA. The surgeon cuts within the coagulated tissue to divide the liver. However, as the device has no cutting ability, the surgeon has to use a separate cutting mechanism, like a scalpel or scissors, to cut within the coagulated tissue to divide the liver. This alternating coagulation and cutting step is continued until the line of transection is completed to divide the liver. However, as the full thickness of the liver parenchymal cannot be completely coagulated in a single attempt due to the length of the RFA needle, it is often very difficult to estimate how deep the avascular plane is after coagulation. Further, one of the other issues with this method is that the surgeon may not know for certain which parts of the liver are still vascular.

Certain embodiments of the present invention reduce the risk of unnecessary cutting of the tissue and extraneous bleeding that may be resulted from unnecessary cutting by employing a blood flow sensing mechanism. The blood flow sensing mechanism senses the amount of blood flow in the tissue prior to cutting the tissue and indicates whether the tissue has been fully coagulated. In certain embodiments, the blood flow sensing mechanism may require zero or negligible blood flow in the tissue in order to declare the tissue as fully coagulated. In certain embodiments, the blood flow sensing mechanism may require the blood flow in the tissue to reach a minimum threshold before declaring the tissue as being sufficiently coagulated or/and ready for cutting. The indication of coagulation may be signaled externally to the operator and/or internally within the device through methods known in the art. For example, the blood flow sensing mechanism may indicate that the tissue has been sufficiently coagulated by activating a visual or an audible signal to the operator. The blood flow sensing mechanism may utilize techniques known in the art to determine the amount of blood flowing in the tissue. For example, in certain embodiments, the blood flow sensing mechanism my employ an ultrasonic Doppler flow detection mechanism to determine the amount of blood flowing in the tissue. In some other embodiments, laser Doppler and/or mechanical sensing of blood flow may be employed. Other embodiments may use any available method in the art to determine blood flow in the tissue.

In some embodiments, the blood flow sensing mechanism may be continually used to determine presence of blood flow in human tissue. The absence of coagulated tissue may serve as an indication for an operator of the device (e.g., surgeon) that a transition from coagulated tissue to healthy tissue has occurred. Available methods in the art may be used to indicate this transition to the operator (e.g., the blood flow sensing mechanism may indicate this transition by outputting an audible or visible signal). Upon observing such signal, the operator may determine if the tissue has been cut and/or resected to a desired level and possibly stop further cutting and/or resection of the tissue. Further, the blood flow sensing mechanism may be used to prevent excessive ablation by early detection of stoppage of blood flow in a biological tissue.

In laparoscopic surgeries, instruments are normally inserted through small incisions made in the body. Therefore, the instruments have restricted degrees-of-freedom compared to open surgeries. The degree-of-freedom is even more restricted in single port laparoscopic operations. Furthermore, single port laparoscopic operations may be troublesome due to proximity of all trocars at the umbilicus and frequent crossing of instrument shafts at point of entry into abdominal cavity which can result in clashing of the surgical instruments. To circumvent this problem, multiple ports (i.e., incisions) in various directions may be placed. However, adding incision sites may increase the amount of trauma to the abdominal wall.

In order to overcome the difficulties resulting from having a restricted degree-of-freedom, certain embodiments of the present invention employ a flexible actuation mechanism that provides the device with at least two degrees-of-freedom. In one embodiment, the flexible actuation mechanism enables the device with translation motion along vertical and horizontal axes. In another embodiment, the first degree-of-freedom provides a translation motion that may be used to penetrate into the tissue. Another degree-of-freedom, a second degree-of-freedom, may provide a translation motion that cuts the tissue. In certain other embodiments, a third degree of freedom, which may be a bending motion, perpendicular to the second degree-of-freedom, may be used to separate the sticky tissue. In certain other embodiments, the flexible actuation mechanism may provide the device with additional degrees-of-freedom by enabling additional translation and/or rotation motions. By increasing the degrees-of-freedom of the device, embodiments of the present invention increase the level to which the resection device may be manipulated.

In some embodiments, electroactive polymers (EAP) may be employed to develop a miniature, lightweight, miser flexible actuator 230 (FIG. 2 discussed later) that can operate similar to that of a biological muscle. See Hunter I W, Lafontaine S. A comparison of muscle with artificial actuators, IEEE Solid-State Sensor and Actuator Workshop, 1992: 677-679; and Yoshiko A, Mochizuki A, Kawashima T, Tamashita S, Asaka K, Oguro K. Effect on bending behavior of counter cation species in perfluorinated sulfonate membrane-platinum composite. Polymers for Advanced Technologies, 1998: 9:520-526 (both herein incorporated by reference).

Embodiments of the present invention further include a retractable cutting mechanism (e.g., knife) with at least two degrees-of-freedom. The term "cutting," as used herein, is a broad term that is used in its ordinary sense, including, without limitation, to refer to a separation of an object or a portion of an object into two or more portions using a force. The terms "cutting mechanism," "knife," "scalpel," and "cutter," as used herein, are broad terms that are used in their ordinary sense, including, without limitation, to refer to a small and sharp bladed instrument used in surgery and/or anatomical dissection. Embodiments of the present invention may utilize any cutting mechanism known in the art. The blades of the scalpel may be made of stainless steel, high carbon steel, titanium, or any other material commonly used in the art.

The force used to actuate the retractable knife may be exerted by a variety of sources, such as an actuator. In certain embodiments, a pneumatic actuator may be used to retract the retractable knife. The insertion force may be created by converting potential energy from the compressed air into kinetic energy. In some other embodiments, springs and/or mechanical actuators, electromechanical actuators or other actuators may be used. Other actuation techniques known in the art may be used.

Certain embodiments of the present invention relate to a single flexible coagulating and cutting device that can simultaneously coagulate, detect complete coagulation, and allow the surgeon to cut the coagulated parenchyma through the same probe. The embodiments utilize a laparoscopic probe that combines a coagulation technology (e.g., the RFA technology) with a cutting mechanism, a blood-flow sensor, and a flexible actuation mechanism to simultaneously coagulate biological tissue, detect the presence/absence of blood flow to confirm avascularity and cut the coagulated tissue.

Embodiments of the present invention eliminate the risk of bleeding due to cutting too deep and reduce the time spent on re-coagulation of coagulated areas, thereby shortening duration of surgery (procedure elapsed time). Reducing the amount of bleeding eliminates the need for blood transfusion. This is beneficial for patients and can reduce demands on blood products supply.

Figure 1A:
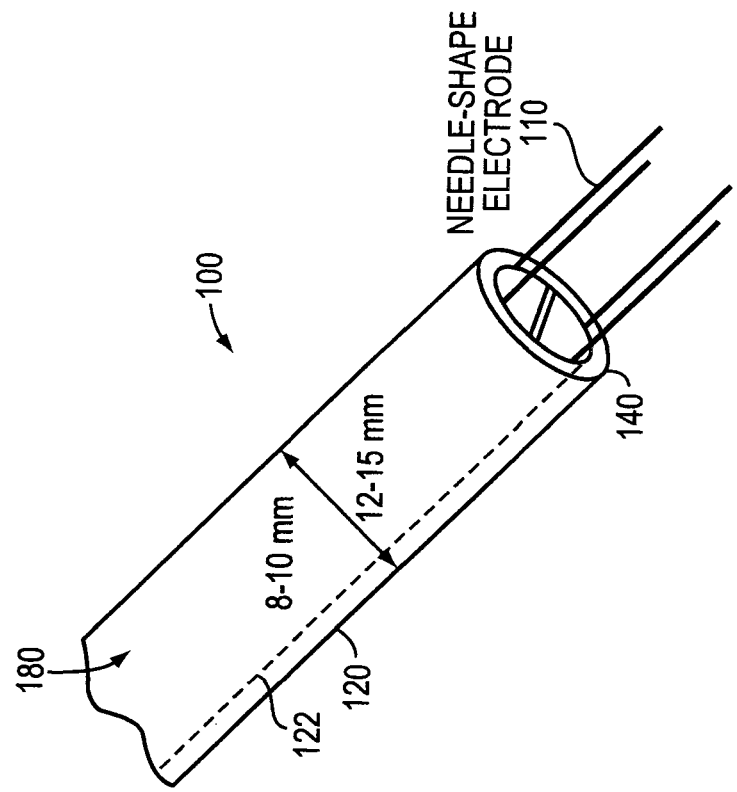

FIGS. 1A-1D illustrate a laparoscopic resection device 100 according to certain embodiments of the present invention. In certain embodiments, the laparoscopic resection device 100 may be formed using one or more concentric cylindrical tubes 120, 122. For example, as shown in FIGS. 1A-1B, the laparoscopic resection device 100 may include two cylinders 120, 122. In some embodiments, the inner cylindrical tube 122 may have a diameter of between 8-12 millimeters and outer cylindrical tube 120 may have a diameter of between 12-15 millimeters. The inner cylinder 122 includes a cutting mechanism (i.e., at least one retractable knife 130) at its distal end 140. The outer cylinder 120 has a hollow core and includes a plurality of needle-shaped electrodes 110 at its distal end 140. The needle-shaped electrodes 110 serve as a plurality of coagulating elements and provide coagulation using available methods in the art.

For example, in one embodiment, the RFA technology may be used to coagulate the tissue between the needle-shaped electrodes 110. Specifically, the electrodes 110 are connected to a Radiofrequency generator. When powered on, the electrodes ablate the neighboring or area tissue. Generally, at about 50° C. to 60° C., the tissue is coagulated. Radiofrequency ablation (RFA) involves the use of high-frequency alternating currents which produce ionic agitation that flows through the needles attached to the probes. The division process is performed after the parenchyma is coagulated by mono-polar or bipolar RF ablation. Pre-coagulation performed in this manner is maximal and complete for each cycle and requires more time and more RF energy than is necessary. The liver surface is cut once the entire transection line has been pre-coagulated and this may result in needlessly coagulated and desiccated margins on the remnant liver.

Radio frequency assisted methods have been widely used in the treatment of cancers, such as liver cancer. During the surgical procedure, Radio-frequency pulses (500 KHz) are used to induce heating and hence coagulation (at about 60° C.) to the tissue and cancerous cells. Another medical procedure, often performed for liver tumors, is a hepatectomy, the resection process of removing partial liver tissue which encapsulates the tumor, from the liver organ. These two processes are often performed separately, with ablation performed first on the desired liver zone and manual resection with surgical scalpel thereafter. Radio frequency may be used to introduce ablation and coagulation to the tissue for minimizing blood loss during the procedure. Certain embodiments incorporate both procedures to enable smooth surgical transition between ablation and resection.

It is understood that other implementations of the plurality of coagulating elements 110 are suitable. For example, the coagulating elements 110 may employ laser technology or certain energy waves. The coagulating elements 110 coagulate target tissue using any of RFA, microwave ablation, cryo ablation, shockwave ablation and high intensity focused ultrasound ablation, or the like.

FIG. 1C illustrates the blood flow sensing mechanism 170. The blood flow sensing mechanism is positioned at the distal end 140 of the laparoscopic resection device 100. The blood sensing mechanism includes a blood flow sensor 170 (also referred to as transducer 170). The transducer may be connected to a signal processing system via a thin twisted pair of power, data, and control signal cables.

In some embodiments, a laser Doppler blood flow sensor may be incorporated to provide feedback information to help determine blood flow and/or whether the tissue has been coagulated appropriately prior to tissue division. A graphic user interface may be used with the device to give a visual signal once an acceptably low blood flow rate is detected.

In certain embodiments, the blood flow sensor 170 may employ a modality such as electrical impedance imaging to determine presence of blood flow.

A completely ablated tissue 190 (e.g., liver tissue) should have zero or negligible blood flow. In some embodiments, any blood flow may be detected by a continuous-wave ultrasoundic Doppler flow detector (not shown). In certain other embodiments, methods known in the art, such as laser and mechanical detection may be used. In one embodiment, a beam of high frequency ultrasound, for example about 3-10 MHz, may be projected through the device 100 on the tissue surface towards the ablated tissue.

In certain embodiments, a lightly loaded lead zirconate titanate transducer 170 with a diameter of approximately 1-2 mm may be used to detect blood flow. Further, in some embodiments, a separate sensing component (of, for example, approximately 1 mm) may be used to detect the ultrasound backscattered from the moving blood within the ablated tissue. The backscattered signal is a Doppler signal shifted by an amount proportional to the velocity of the scatterers moving through the sound field. The intensity of the backscattered signal corresponds to the spectrum of velocity of blood flow. A zero or negligible intensity may be used as an indicator of zero or negligible blood flow 195 to declare the target tissue as completely ablated tissue.

The division and blood flow sensing mechanisms may be interchangeable in the apparatus. Further, the directional information of the blood flow is not required.

In certain embodiments, upon detection of blood flow 195 in the tissue, the needle-shaped electrodes 110 may be used to coagulate the tissue. In some embodiments, the blood flow sensing mechanism 170, upon detection of blood flow, indicates the presence/absence of blood flow by issuing a signal, such as an audible and/or visual signal, and prompts the operator and/or device to begin coagulating the tissue using the needle-shaped electrodes 110.

Next, in one embodiment, when the tissue is fully ablated and blood flow is sufficiently low, the device 100 provides a visual signal to the surgeon to commence resection (cutting). In embodiments, the device may also at that time signal to the surgeon to (or automatically) discontinue ablation for the time being by discontinuing to power coagulating elements 110. This prevents against excessive ablation. Cutting may be performed with a retractable knife driven by an air cylinder connected to a solenoid valve and air compressor. The solenoid valve can be toggled open and closed by a switch on the device handle to actuate the knife blade 130 forward. The knife 130 may be retracted by means of a spring built into the air cylinder as a self-retracting mechanism.

As shown in FIG. 1B, a retractable knife 130 may be actuated by an actuator 230 (FIG. 2), such as a pneumatic actuator (not shown). The pneumatic actuator is a mechanical device that produces insertion force and movement driven by compressed gas. The insertion force is created by converting potential energy from the compressed air into kinetic energy.

In some embodiments, the actuator may be activated upon detection of coagulated tissue by the blood flow sensing mechanism 170 to drive the retractable knife 130 and cut the target tissue. The actuator and the retractable knife 130 continue to cut the coagulated tissue until the tissue has been cut to desired dimensions and/or the presence of non-coagulated tissue is detected by the blood flow sensing mechanism 170. Blood flow sensing mechanism 170 continuously senses blood flow levels of the target tissue.

The desired dimension or depth of cutting may be defined by an operator/clinician. Alternatively, the depth may be determined via the measurement from the blood flow sensor 170. The sensor 170 can measure the blood flow at various depths, and remember the deepest and safest cut. In some embodiments, a close loop mechanism may be deployed to track the force feedback on the knife 130 to determine if the tissue is not coagulated.

The pneumatic actuator driving the retractable knife 130 provides the device 100 with at least two degrees-of-freedom. Specifically, movements of the pneumatic actuator may translate the retractable knife 130 along vertical 150 (first degree-of-freedom) and horizontal 160 (second degree-of-freedom) directions. The first degree-of-freedom 150 may be used to penetrate the ablated tissue controlled by a releasing mechanism (not shown). The second degree-of-freedom may be a translational motion that cuts the tissue. In some embodiments, a third degree-of-freedom (not shown) which is a bending motion perpendicular to the second degree-of-freedom may further be used to completely separate the "sticky" tissue. In such embodiments, the surgeon may have control over the depth of penetration and the length of cutting. As the surgeon is holding the proximal end 180 of the device (about 20-25 cm away from the needle-shaped electrodes 110), there is a hand-piece to control the knife releasing mechanism (actuator 230) and knife 130 movements at the opposite end 140.

In some embodiments, a micro-actuator and encoder assembly (not shown) may also be housed in the proximal end 180. The two ends of the apparatus 140, 180 may be connected via a very thin stainless steel cable (not shown). This push-pull cable has a 0.5 millimeters external diameter and an inner wire of 0.4 millimeters.

Further, in certain embodiments, customized software and/or signal processing techniques known in the art may be used to provide the laparoscopic liver resection device 100 with additional control. The digital signal processing unit may be connected to the proximal end 180 of the apparatus. For example, a closed loop control of device 100 may be programmed or otherwise configured to timely stop ablation activity by discontinuing operation of coagulating elements 110 on the target tissue upon blood flow sensor 170 sensing insufficient or no blood flow in the target tissue. Such a closed loop control provides a bloodless tissue/organ division method and system 100 that prevents against excess ablation.

FIG. 1D is an example of an embodiment of the present invention that includes blood flow sensing 170 and cutting mechanisms 130 in one cylindrical device 100. Specifically, the distal end 140 of the device is shown. Although the combined sensing 170 and cutting mechanism 130 (with actuation 230 and release controller) may involve some dedicated assembly process, nevertheless, it may be more convenient for the surgeon using the device.

Embodiments of the present invention may be used to determine the optimal ablation, blood flow sensing and cutting processes for prototype devices. The tissue deforms due to the tissue denaturalization and interaction with the surgical devices.

The integration of ablation, sensor and division mechanisms into a single device has the potential to reduce operative time and minimize trauma. Resection can be performed with a single insertion of the device. The laser Doppler blood flow sensor is used for continual feedback because the blood flow is low in fully coagulated tissues. This helps the surgeon to determine whether the tissue is properly coagulated before division. This real-time feedback mechanism minimizes live tissue damage by eliminating the application of unnecessary RF. In addition, the protrusion of the cutting mechanism 130 is designed to ensure that the resection is undertaken only in properly coagulated tissue, thereby minimizing bleeding caused by overcutting.

Figure 2:
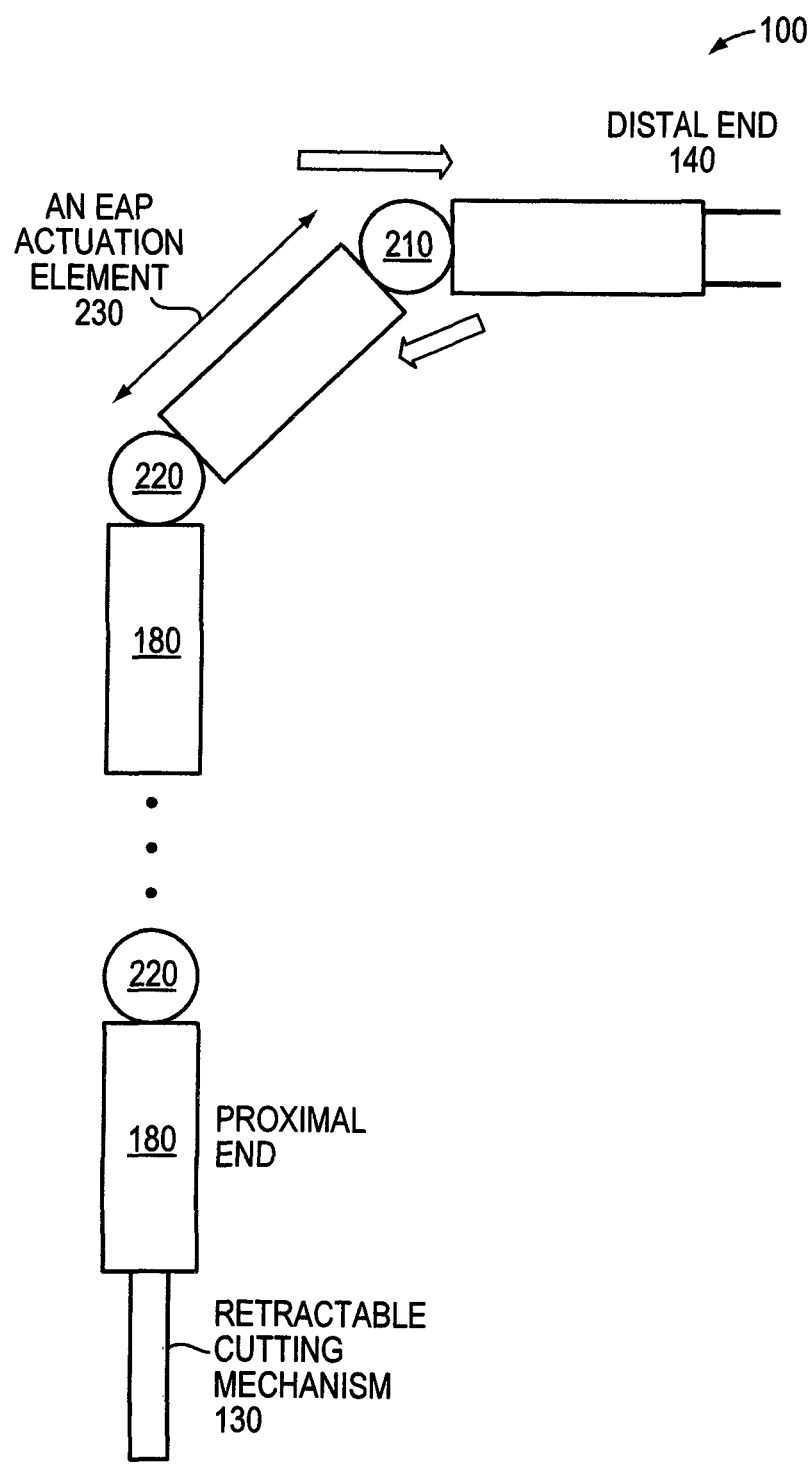
FIG. 2 is an illustration of a flexible actuation mechanism according to certain embodiments of the present invention.

FIG. 2 illustrates a flexible actuation mechanism according to certain embodiments of the present invention. Computational intelligence may be included in this apparatus to significantly advance access and integrated ablation and cutting processes. The smart device may help precisely determine the completion of the ablation process by estimating the presence of blood flow and automate the cutting process.

As described above, the flexible actuation may be provided by one or more EAP actuation elements 230. Specifically, the EAP may bend back and forth to change the direction of the distal end 140. When using more than one actuation elements, the device 100 (FIGS. 1A-1D) may be able to reach regions of interest that are difficult or nearly impossible to access.

In certain embodiments, a modular structure may enable a user to customize the work space of the device in accordance to the patient and the procedure at hand. For example, a typical implementation of the bending EAP actuator 230 includes ion exchange membrane metal composites. Since the material is sensitive to water content inside its porous matrix, effective coating is required to protect the material from water loss through evaporation. The coating is also required for the power and signal cables as well as the gas transmission cable between the proximal and distal ends 180, 140. The ionomer may be driven by 2.5 Volts. This small voltage is safe for human beings and may be delivered via dendritic cells (DC).

In certain embodiments, the flexible mechanism 230 may also be implemented via mechanical means with pre-shaped linkages 210, 220. For example, in one embodiment, the linkages 210, 220 may be spherical elements on which the proximal end 180 rotates. The pre-shaped linkages provide the device with added degrees-of-freedom and increase the flexibility of the device.

Other embodiments may include robotics, closed loop feedback, other control(s) and the like. See Leong, F., et al., "A Precise Robotic Ablation and Division Mechanism for Liver Resection," *Lecture Notes in Computer Science*, 5128: 320-328 (2008) herein incorporated by reference.

While this invention has been particularly shown and described with references to example embodiments thereof, it will be understood by those skilled in the art that various changes in form and details may be made therein without departing from the scope of the invention encompassed by the appended claims.

What is claimed is:

1. A device, comprising:
    a plurality of coagulating elements for coagulating target tissue of a biological body;
    a blood flow sensor for sensing levels of blood flow within the target tissue, the blood flow sensor capable of indicating absence of blood flow when the target tissue is substantially coagulated;
    a retractable cutter for cutting the coagulated tissue in an event the sensor indicates absence of blood flow in the target tissue;
    an actuator coupled to the retractable cutter for activating the retractable cutter;
    a housing at a distal end of the device housing at least the plurality of coagulating elements and the retractable cutter; and
    wherein the blood flow sensor is capable of continuing to sense levels of blood flow in the tissue after indicating absence of blood flow and the actuator is capable of actuating the retractable cutter away from live tissue in an event where the sensor indicates presence of blood flow within the tissue.

2. The device of claim 1 wherein the blood flow sensor indicates the absence of blood flow in an event where zero blood flow within the target tissue is observed.

3. The device of claim 1 wherein the blood flow sensor indicates the absence of blood flow in an event the blood flow observed within the target tissue is less than a predetermined threshold.

4. The device of claim 1 wherein the blood flow sensor indicates the absence of blood flow within the target tissue by evaluating intensity of a backscattered signal resulting from irradiating the tissue with an ultrasonic wave.

5. The device of claim 1 wherein the blood flow sensor indicates the absence of blood flow within the target tissue by evaluating intensity of a backscattered signal resulting from analyzing the tissue using at least one of an ultrasonic wave, a shock wave, mechanical tissue properties, and electrical impedance imaging.

6. The device of claim 1 wherein the actuator includes at least one of a pneumatic actuator, a spring, an electro-chemical actuator, an electromechanical actuator and a mechanical actuator.

7. The device of claim 1 wherein the retractable cutter includes at least one of a retractable knife or a retractable scalpel.

8. The device of claim 1 wherein the actuator employs one or more electroactive polymers (EAP) actuation elements.

9. The device of claim 1 wherein the distal end is coupled with at least one flexible structure, the flexible structure providing the distal end with movement in two or more degrees-of-freedom.

10. The device of claim 9 wherein the flexible structure is spherical.

11. The device of claim 1 wherein the plurality of coagulating elements employ any of electrodes, lasers and certain energy waves.

12. The device of claim 1 wherein the plurality of coagulating elements coagulates the target tissue using at least one of Radiofrequency Ablation (RFA), microwave ablation, cryo ablation, high intensity focused ultrasound ablation, and shockwave ablation of the tissue.

13. A method for dividing a biological tissue, comprising:
coagulating target tissue of a biological body;
sensing absence of blood flow within the target tissue and indicating the sensed absence of blood flow;
cutting the coagulated target tissue; and
continuing to sense blood flow within the target tissue after indicating the absence of blood flow and indicating if the presence of blood flow is sensed.

14. The method of claim 13 further including indicating the sensed absence of blood flow in an event where zero blood flow within the tissue is observed.

15. The method of claim 13 further including indicating the sensed absence of blood flow in an event the blood flow observed within the tissue is less than a predetermined threshold.

16. The method of claim 13 further including indicating the sensed absence of blood flow within the tissue by evaluating intensity of a backscattered signal resulting from irradiating the tissue with an ultrasonic wave.

17. The method of claim 13 further including indicating the sensed absence of blood flow within the tissue by evaluating intensity of a backscattered signal resulting from analyzing the tissue using at least one of an ultrasonic wave, a shock wave, mechanical tissue properties, and electrical impedance imaging.

18. The method of claim 13 further including coagulating the tissue using at least one of Radiofrequency Ablation (RFA), microwave ablation, cryo ablation, high intensity focused ultrasound ablation, and shockwave ablation of the tissue.

19. The method of claim 13 further comprising:
wherein upon sensing absence of blood flow within the target tissue, discontinuing the step of coagulating target tissue.

* * * * *